US010874289B2

(12) United States Patent
Hale (10) Patent No.: US 10,874,289 B2
(45) Date of Patent: Dec. 29, 2020

(54) CONTROL INTERFACE AND ADJUSTMENT MECHANISM FOR AN ENDOSCOPE OR EXOSCOPE (71) Applicant: Karl Storz Imaging, Inc., Goleta, CA (US)

(72) Inventor: Eric Hale, Goleta, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 521 days.

(21) Appl. No.: 15/656,158

(22) Filed: Jul. 21, 2017

(65) Prior Publication Data

US 2019/0021576 A1    Jan. 24, 2019

(51) Int. Cl.
*A61B 1/005* (2006.01)
*A61B 1/00* (2006.01)
*A61B 1/045* (2006.01)
*A61B 34/00* (2016.01)
(Continued)

(52) U.S. Cl.
CPC ........ *A61B 1/0052* (2013.01); *A61B 1/00006* (2013.01); *A61B 1/00039* (2013.01); *A61B 1/00066* (2013.01); *A61B 1/00068* (2013.01); *A61B 1/00158* (2013.01); *A61B 1/045* (2013.01); *A61B 1/05* (2013.01); *A61B 1/0661* (2013.01); *A61B 34/73* (2016.02); *A61B 34/74* (2016.02); *A61B 1/00188* (2013.01); *A61B 2034/731* (2016.02); *A61B 2034/742* (2016.02)

(58) Field of Classification Search
CPC ............ A61B 1/00039; A61B 1/00043; A61B 1/00052; A61B 1/00066; A61B 1/00006; A61B 1/00147; A61B 1/00158; A61B 1/005; A61B 1/0051; A61B 1/0052; A61B 1/0053; A61B 1/0055; A61B 1/0056; A61B 1/0057; A61B 1/0058; A61B 1/00183; A61B 1/00188; A61B 1/0019; A61B 2017/00212; A61B 5/7475; A61B 34/73; A61B 34/74; A61B 2034/741–744; A61B 2034/731–733
See application file for complete search history.

(56) References Cited

U.S. PATENT DOCUMENTS

3,557,780 A   1/1971   Sato
5,762,603 A   6/1998   Thompson
(Continued)

*Primary Examiner* — Ryan N Henderson
(74) *Attorney, Agent, or Firm* — Muncy, Geissler, Olds & Lowe, P.C.

(57) ABSTRACT

A control interface and adjustment mechanism for an endoscope including multiple buttons, each button including a touch surface and a magnet disposed below the touch surface. The control system of the control interface includes a magnetometer detecting ambient magnetic fields and a control processor receiving signals from the magnetometer, wherein the control processor is connected to at least one endoscope component and controls the at least endoscope component. The control processor filters received first field information from the magnetometer to determine if the received first field information matches a specific stored button vector of at least one button vector stored in memory, and if the received first field information matches the specific stored button vector, then the at least one endoscope component is controlled based on the first information detected by the control unit.

18 Claims, 4 Drawing Sheets (51) Int. Cl.
*A61B 1/05* (2006.01)
*A61B 1/06* (2006.01)

(56) References Cited

U.S. PATENT DOCUMENTS

| | | | | |
|---|---|---|---|---|
| 7,278,965 B2* | 10/2007 | Shimizu | ............. | A61B 1/00163 |
| | | | | 335/205 |
| 2005/0059858 A1 | 3/2005 | Frith et al. | | |
| 2010/0168723 A1* | 7/2010 | Suarez | ................... | A61B 34/30 |
| | | | | 606/1 |
| 2012/0277534 A1* | 11/2012 | Masaki | ............. | A61B 1/00039 |
| | | | | 600/145 |
| 2013/0324978 A1* | 12/2013 | Nicholas | ................ | F16H 25/20 |
| | | | | 606/1 |
| 2014/0188091 A1* | 7/2014 | Vidal | ..................... | A61B 17/00 |
| | | | | 606/1 |
| 2016/0118201 A1* | 4/2016 | Nicholas | ................. | H01H 9/26 |
| | | | | 200/43.17 |
| 2017/0078583 A1* | 3/2017 | Haggerty | ........... | A61B 1/00096 |
| 2017/0112519 A1* | 4/2017 | Inoue | ................ | A61B 17/2909 |
| 2020/0271479 A1* | 8/2020 | Wang | ..................... | G01D 5/145 |

* cited by examiner

CONTROL INTERFACE AND ADJUSTMENT MECHANISM FOR AN ENDOSCOPE OR EXOSCOPE

BACKGROUND OF THE INVENTION

Field of the Invention

The invention relates to a manual control system for endoscopic cameras, and peripherals. Particularly, functional control is provided through a combination of buttons accessible to the user.

Description of the Background Art

Optical instruments such as endoscopes, borescopes, and exoscopes may include an electronic imaging device located, for example, at a proximal end of an elongated shaft or in a camera head which is connected to an elongated shaft. In addition, the distal end of the elongated shaft can contain focusing or zoom lenses and a light source. The distal end often requires manual control for the lenses and sometimes requires manual control for direction of view if the distal end is flexible.

In particular, a standard rigid endoscope has a distal objective, a proximal eyepiece, a proximal camera detachably connected to the endoscope with the zoom being performed in the camera, and with the buttons on the camera. Alternatively, a rigid video endoscope can have a distal objective and distal image sensor(s) or a distal objective and proximal image sensors (using a rod lens system) such that the buttons are on the handle of the proximal end of the endoscope. Additionally, a flexible video endoscope with a distal objective, LED, and image sensor can have the buttons on the proximal handle. Finally, an exoscope would have an objective and camera with a separate button module for camera or light control.

Originally, the control of endoscopes was purely mechanical as in the U.S. Pat. No. 3,557,780 to Masaaki Sato, which discloses tension wires to steer a flexible head of the endoscope. The control interface of Sato is a rotating knob, which provides angular control for the deflection of the imaging head of the endoscope. The camera disclosed in this device is film based and requires actuation and lighting as well.

Cameras and control interfaces then became digital as in U.S. Pat. No. 5,762,603 to Robert Lee Thompson where foot pedals provide control of the digital camera head and lighting module. The foot pedal control assembly includes four controls: (1) moving camera housing left and right; (2) moving camera housing up and down; (3) zooming in and out; and (4) adjusting light intensity up and down. Signals from the foot pedal control assembly are routed to the control console for translation and transmission to the camera head.

In the endoscopes of Sato and Thompson, the camera head is disposed at the proximal end of the endoscope. This placement, however, limits the size of the CCD imaging chip and also requires compact lens arrangements for zoom and focus. Alternatively, cameras, focusing optics and zoom optics can be arranged at a distal end of the endoscope opposite the insertion end with the imaged light being carried from the insertion end by carrier lenses. This configuration allows the control interface to be adjacent to the camera and optics being controlled.

The control interface must give the user tactile feedback since the user often cannot give full attention to the buttons being pushed. Therefore, touchscreens and the like cannot be used for the control interface. Furthermore, the camera heads for endoscopes are subjected to repeated exposure to chemicals and fluids for sterilization and cleaning. As a result, traditional push buttons and electronic contacts cannot be used.

Figure 1:
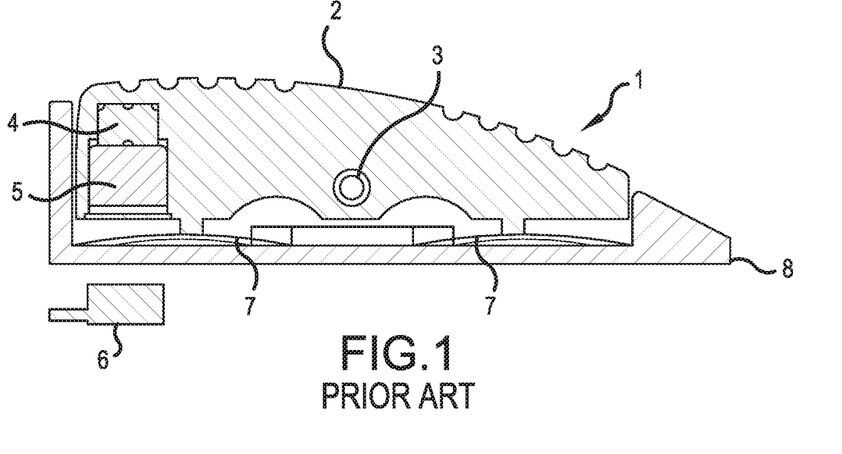
FIG. 1 is a conventional rocker switch.

Some endoscope control interfaces, such as Frith, et al. (US 2005/0059858), utilize hall proximity sensors inside the camera module coupled with movable magnets that actuate the hall proximity sensors. FIG. 1 of illustrates a rocker switch 1 as disclosed in the conventional art, namely, Frith and provides leaf springs 7 below a front and back of one button 2 so that forward or backward pressure by a user is translated into proximity signals for control of the camera. The hall sensor 6 detects the up and down movement of the magnet 5 and magnetic pin 4 as the button 2 pivots about a central support 3. The switch components in Frith are all disposed outside a sealed endoscope housing 8 as described previously.

The rocking motion and resistance of the leaf springs provides tactile feedback for control of a one dimensional forward and backward movement. The rocking switch of Frith is limited to control in one direction for one component. Therefore, the switch can only control simple actions such as zoom or focus, but cannot pan across a view, control a proximal end of the endoscope, or shift lighting directions. Furthermore, the device of Frith does not compensate for orientation of the endoscope. In other words, the endoscope can be inserted and positioned in a number of directions and also rotated about its axis. If left uncorrected, these movements degrade the viewing experience of the surgeon or user.

Systems like Frith that use a magnet/hall sensor pairing do not utilize a magnetometer for orientation. In particular, the button magnets interfere with magnetometer-based orientation systems and oversaturate the natural magnetic field strength. Therefore, orientation systems are not paired with sealed hall magnet button interfaces due to this interference. The system shown in FIG. 1 illustrates a conventional control button for an endoscope. Conventional hall magnet/button switches double the number of parts needed for a single button, and therefore, are costly and difficult to manufacture.

Thus, control interfaces for medical devices require special design considerations. In addition, a surgeon must be able to perform at least the four adjustments described in regards to the device of Thompson above. The current control interfaces available are limited in adaptability and do not provide integrated control of all endoscope functions.

SUMMARY OF THE INVENTION

In view of the foregoing and other exemplary problems, drawbacks and disadvantages of the conventional methods and devices, an exemplary feature of the present invention is to provide a control interface, and method, for endoscopes and cameras that use an orientation tracking system.

In an exemplary non-limiting aspect of the invention a control interface and adjustment mechanism for an endoscope, comprises at least one button or more than one button and has a touch surface, a magnet disposed below the touch surface, a magnetometer detecting ambient magnetic fields, and a control processor receiving signals from the magnetometer. The control processor is connected to at least one endoscope component and controls the at least endoscope component. The control processor filters received first field information from the magnetometer to determine if the received first field information matches a specific stored button vector of at least one button vector stored in memory, and if the received first field information matches the specific stored button vector, then the at least one endoscope component is controlled based on the first information detected by the control unit.

A control interface and adjustment mechanism for an endoscope or exoscope is provided that includes at least one button or more than one button with a touch surface and a magnet disposed adjacent to the touch surface of the button, a magnetometer detecting ambient magnetic fields, and a control processor receiving signals from the magnetometer, the control processor being connected to at least one peripheral component and controls the at least one component, the control processor filtering received first field information from the magnetometer to determine if the received first field information matches a specific stored button vector of at least one button vector stored in memory, and if the received first field information matches the specific stored button vector, the at least one peripheral component is controlled based on the first field information received by the control processor. The endoscope includes gyroscope and an accelerometer connected to the control processor with the gyroscope providing orientation signals to the control processor, and the orientation signals being corrected based on ambient magnetic fields detected by the magnetometer.

In an exemplary embodiment of the invention a method of controlling an optical component is provided that comprises receiving, at a control unit, orientation data from a magnetometer; filtering the received orientation data based on past orientation data, matching the received orientation data in real time based on a delta function stored in memory, the delta function mapping a magnetic field shift to an expected magnetic field shift for a button, signaling an input of the button to the control unit, if a detected magnetic field shift matches the expected magnetic field shift, and controlling a peripheral device based on the input of the button.

In an exemplary embodiment of the invention an endoscope includes a sealed housing, a control interface and adjustment mechanism, including at least two buttons, each of the at least two buttons including a touch surface and a magnet disposed adjacent to the touch surface. The endoscope also including magnetometer detecting ambient magnetic fields and a control processor receiving signals from the magnetometer, the control processor being connected to at least one endoscope component and controlling the at least one endoscope component, the control processor filtering received first field information from the magnetometer to determine if the received first field information matches a specific stored button vector of at least one button vector stored in memory, and if the received first field information matches the specific stored button vector, the at least one endoscope component is controlled based on the first field information received by the control processor.

The endoscope can additionally include a gyroscope and an accelerometer connected to the control processor, wherein the gyroscope provides orientation signals to the control processor, wherein the orientation signals are corrected based on ambient magnetic fields detected by the magnetometer.

The specific stored button vector is an average magnetic field shift for each button so that the average magnetic field shift is mapped to the first field information by a delta function. The average magnetic field shift is mapped to the first field information by the delta function based on orientation data received at the control processor from a gyroscope and/or an accelerometer. If the first field information does not match the specific stored button vector, then the first field information is ignored or interpreted as movement of the endoscope or exoscope. The specific stored button vector can be an average magnetic field shift calculated from multiple button depressions detected when the magnetometer is in a calibration position.

The magnet of the each button is depressed when the touch surface is pressed by a user, the magnet being depressed such that the magnetometer detects a magnetic field shift as part of the first field information. The endoscope can have a second button, such that the first button and second button have corresponding specific stored button vectors. If the at least one button and second button are activated substantially simultaneously, the control processor determines that the two buttons were pressed by matching a sum of the specific stored button vector for each button with the first field information. The specific stored button vector is an average magnetic field shift for one of the two buttons, such that average magnetic field shift is mapped to the first field information by a delta function based on the orientation data.

The at least one peripheral component can include: a camera of the optical instrument, an internal lighting system, an external lighting system, an image storage system, a CCD/CMOS sensor, a zoom lens, a zoom actuator, a focus lens, a focus actuator, a camera panning motor, an irrigation pump, and/or a moveable camera head. In addition, the buttons can be disposed entirely outside the sealed housing.

The present invention provides an interface with fewer parts and easier assembly than the conventional art. Furthermore, by calibrating the response detected for each button, the influence of ambient magnetic fluctuations can be minimized. Prior art Hall sensors would be activated by magnets or fields not associated with the buttons. Finally, the sealed interface and housing allows for easy cleaning and protection of the electronics in the camera head of the endoscope.

Further scope of applicability of the present invention will become apparent from the detailed description given hereinafter. However, it should be understood that the detailed description and specific examples, while indicating preferred embodiments of the invention, are given by way of illustration only, since various changes, combinations and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION

Referring now to the drawings, and more specifically, FIGS. 2-7, there are shown exemplary embodiments of the method and structures according to the present invention.

Figure 2:
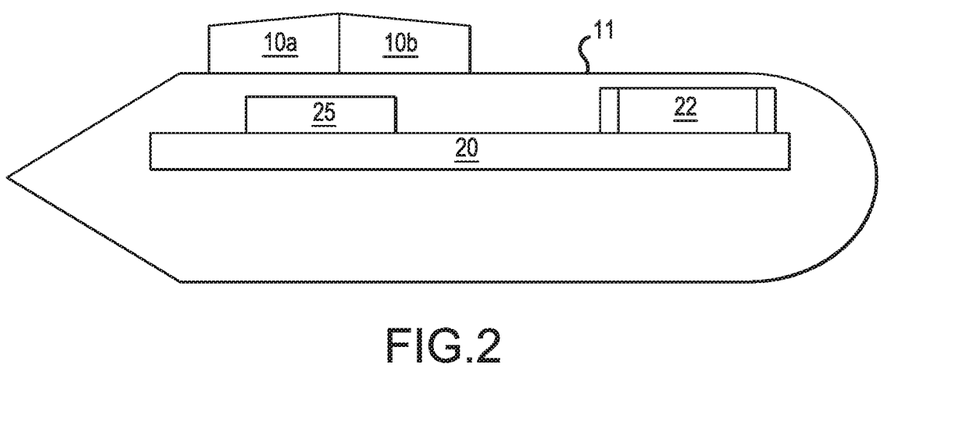
FIG. 2 is a cross-section view of the button interface according to an exemplary embodiment.

The exemplary endoscope head shown in FIG. 2 includes two magnetic buttons 10a and 10b disposed outside a housing 11 of the endoscope. Inside the endoscope head is a printed circuit board including an inertial measurement unit (IMU) 22 and a control processor 25 for interpreting the signals from the IMU 22. The terminating shape at the left-hand end (insertion end) of the housing is purely exemplary and would instead likely extend to another rounded end or other shape.

Figure 3:
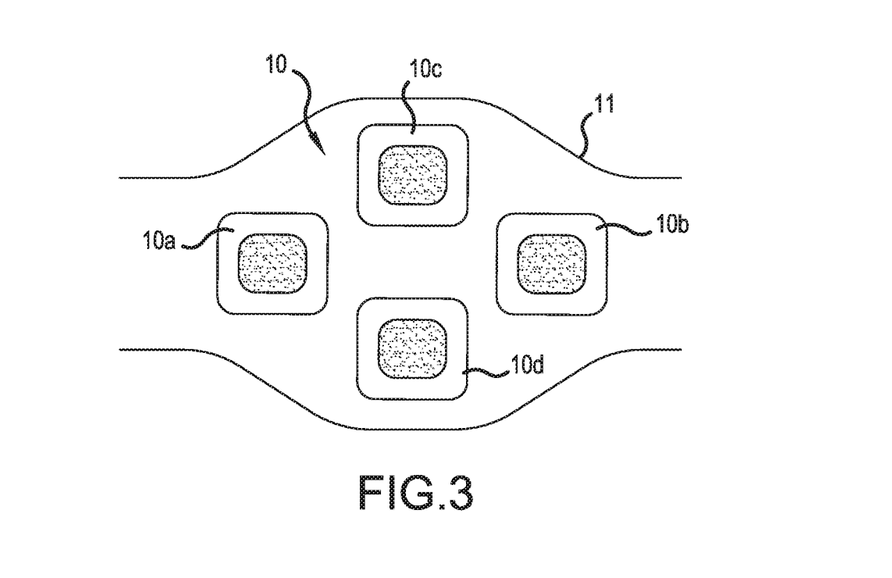
FIG. 3 is a top view of the button interface according to an exemplary embodiment of the present invention.

FIG. 3 illustrates an exemplary button interface shown including four buttons 10a, 10b, 10c, and 10d in a cross configuration. Each of the buttons 10 is preferably a push button with a hard plastic center and a flexible, sealed rubber connection to the endoscope housing 11. The four buttons 10 can control a camera or moveable endoscope head. Specifically, buttons 10c and 10d can provide digital panning or steering a moveable camera head to left and right, and buttons 10a and 10b can provide zoom control or digital panning up and down within a larger captured image.

Additional buttons can be added to provide switching between functionality, for instance switching between steering and panning or switching between zooming and focus. The additional buttons can record a still image from the video recorded by the camera head, or they can be programmable and control another device such as a light source or irrigation pump. Each of the buttons includes a magnet preferably inset in the hard plastic portion of the button such that when the button is depressed the magnet is moved closer or is shifted relative to a detector below the button.

Figure 4:
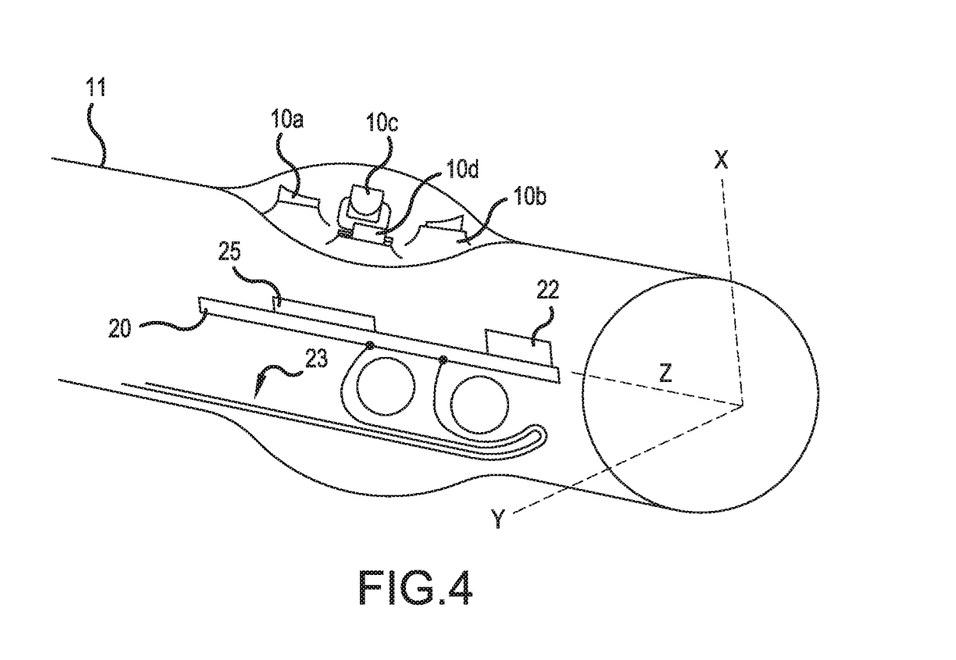
FIG. 4 is a cross-section view of an endoscope handle with a control interface according the embodiment in FIG. 3.

The four buttons are preferably inset in a depressed and widened portion of the endoscope handle as shown in the side view of FIG. 4. Inside the endoscope housing 11 a circuit board 20 is provided. The circuit board 20 includes a control processor 25 and an inertial measurement unit (IMU) 22 including a magnetometer, gyroscope and at least one accelerometer. The two button design of FIG. 2 can include all the features shown and described with respect to FIG. 4 as well.

The circuit board 20 is connected by wires 23 to controllable peripheral components that can be arranged within or externally or connected wirelessly to the endoscope or exoscope, the peripheral elements include, for example, CCD/CMOS sensors, zoom lenses or actuators, focus lenses or actuators, camera panning motors, lighting systems, irrigation pumps or moveable camera heads, for example. The IMU 22 is aligned parallel to a Z-axis projected through the center of the endoscope housing 11.

The inertial measurement unit (IMU) 22 measures rotation of the endoscope housing 11 using the Earth's magnetic field detected by the magnetometer as a reference. The IMU 22 can be mounted inside the hollow endoscope housing 11 such that the IMU is equidistant from the cylindrical sides of the endoscope. This placement ensures accurate measurement of rotations about the Z-axis.

The control processor 25 receives the IMU 22 outputs, and then applies filters and calibrations to these signals. Specifically, the control processor 25 checks if a detected shift in magnetic field direction is the result of a button press. If the control processor 25 determines that a button has been pressed, then the detected shift is discounted and no control adjustments are made for the shift in magnetic field. The control processor 25 then determines which button was pressed based on the detected shift in magnetic field and generates a signal for control of peripheral systems.

Figure 5:
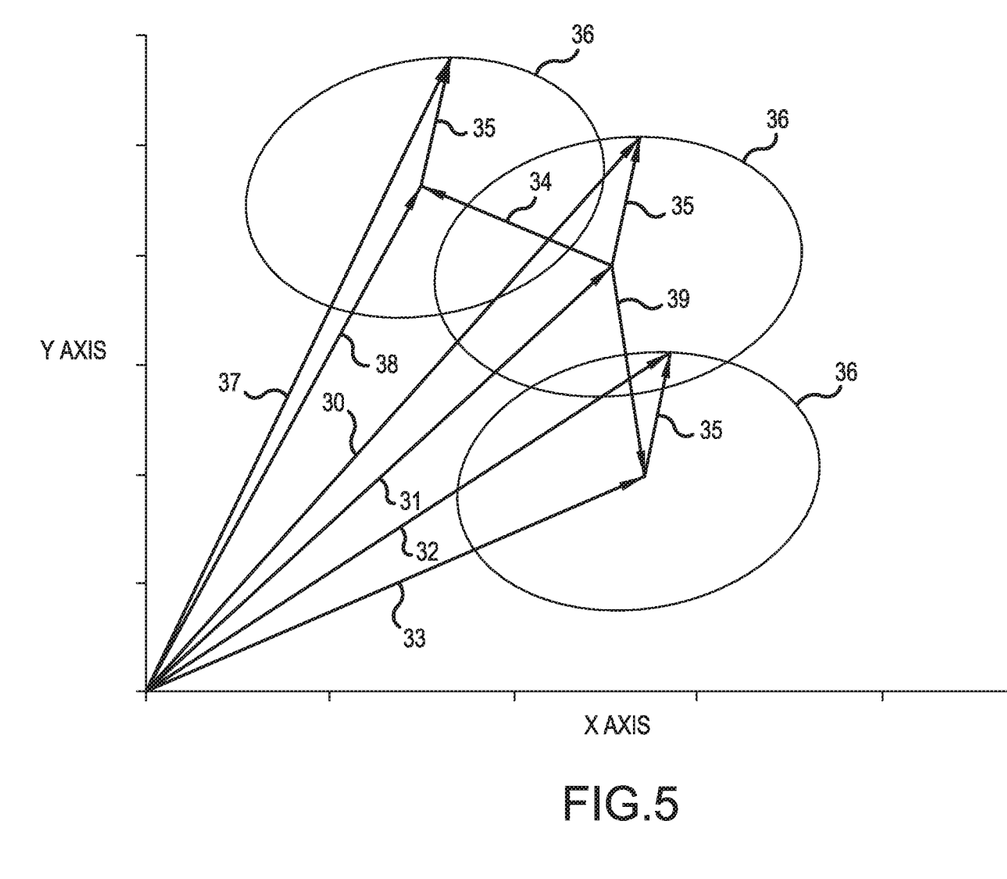
FIG. 5 is a graph illustrating various adaptations to button movements and orientation changes as detected by the control interface.

The determination process is shown in FIG. 5 where exemplary magnetic field vectors, detected by the magnetometer, are shifted in different directions by buttons and rotation of the housing. Vector 31 is a reference magnetic field of the Earth used for calibration when the camera head is turned on. The dark vector 30 is the measured vector when no buttons have been pressed but the endoscope has been rotated about the Z-axis. The rotation causes a shift in the detected magnetic field of the Earth 35 and corresponding gyroscope and accelerometer changes. Vectors 35 are the Earth's magnetic field contribution derived from the difference of the last valid sampling. This changed orientation vector 31 is then stored as the new orientation of the endoscope housing and the change is used to control peripheral devices or the camera display. The lighter circles 36 represent the locus on which the new vector must end based on the calibrated Earth's magnetic field vector.

The magnetic field also shifts when one of the buttons is actuated. For example, when a first button is pushed the magnetic field shifts to vector 33 by vector 39. Alternatively, when a second button is pushed the magnetic field shifts to vector 38 by vector 34. When the magnetic field shifts to vectors 38 or 33, the IMU does not sense any corresponding gyroscope or accelerometer changes. Thus, if the IMU senses magnetic field changes without other motion systems activating, then the magnetic field shift is interpreted as a button press. The magnetometer measurements are sensitive to the outside environment, so the IMU filters for changes in the measurement resembling a calibrated value beyond the inputs from the gyroscope and accelerometer. If a button is pressed while the endoscope is being rotated, the IMU checks why the magnetometer does not match the gyroscope and accelerometer inputs, and determines which button was pressed. If the resulting output does not match a known vector for the button, then the detected shift not supported by the gyroscope or accelerometer can be discarded.

Using the last recorded vector of the Earth's magnetic field 30 and the known deflection 34 or 39 due to the pressing of the specific button, the deflected vectors 33 and 38 are expected to be vectors 32 and 37. If vectors 32 and 37 are actually detected at the magnetometer, then the control processor can determine which button has been pushed. The rotation shift of vector 35 can be removed and the simple shift of vectors 39 and 34 are matched with a calibrated button press vector associated with each button.

The magnetometer can be used to remove long term drift from the gyroscope sensor by adding realignment terms based on the average drift and/or a measured magnetic field calibration point. In addition, this realignment can be calculated in reverse such that changes in the magnetometer outside of values expected by the gyroscope and accelerometer can be identified. These identified anomalous changes are then matched to calibrated magnetic button movements to confirm that the vector change is similar. In particular, the calibrated magnetic button movement can be calculated from an average magnetic field shift of a number of presses and an expected delta function in the magnitude of the average shift depending on orientation. Then, by comparing the real world anomalous change with the expected value from the delta function, the magnetic button input is determined in real time. The delta function is non-spherical.

The final vectors 37 and 32 can be saved as representing the filtered magnetic field of the Earth for future reference by the control processor 25. This filtered magnetic field is useful if another button is pressed while the first button remains pressed. Then, rather than determining a combination vector for both buttons, which can be complicated, the system can determine the vector shift for only the additional button using the final vectors 32 and 37 as a baseline.

FIG. 5 illustrates the filtering process for two buttons using known magnetic field references 30 and 31, and known deflections corresponding to each button being pushed 34 and 39. Additional buttons and different configurations of buttons relative to the magnetometer can be provided with only a few additional calibration steps to determine each button's deflection vector. In addition, once the deflection vector for each button has been recorded, any field shifts that do not correspond to a recorded deflection or combination of deflections can be determined to be a rotation or movement of the endoscope housing or ignored as ambient magnetic fields.

The detected deflections can be compared with known field shifts due to various buttons being pushed, or in the case of multiple buttons, compared with sums of known deflections. Alternatively, each deflection combination from two or more buttons being pressed and each deflection from individual buttons can be separately recorded and calibrated. Based on these calibrated vectors, the magnetic field shifts with no corresponding detection by the gyroscope or accelerometer of the IMU 22 can be assigned to specific buttons being pressed or filtered out.

Figure 6:
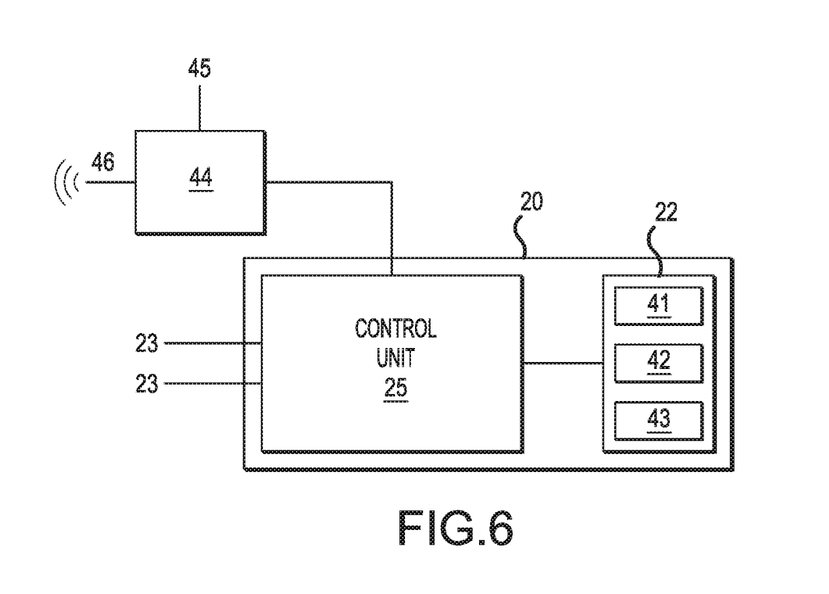
FIG. 6 is a system diagram of the control interface and peripheral devices according to an exemplary embodiment of the present invention.

The system diagram in FIG. 6 shows the control unit 25 on the circuit board 20. The control signal wires 23 transmit the output of the control unit 25 to peripheral devices. In addition, the control unit 25 is connected to the IMU 22, which includes at least one gyroscope 41, at least one magnetometer 42, and at least one accelerometer 43 for measuring changes in the orientation of the endoscope. The control unit 25 is also connected to a graphics processor 44, which receives the recorded camera images and manipulates them for transmission to the user. This transmission from the endoscope can be wireless via antenna 46 or hardwired via wire 45.

Figure 7:
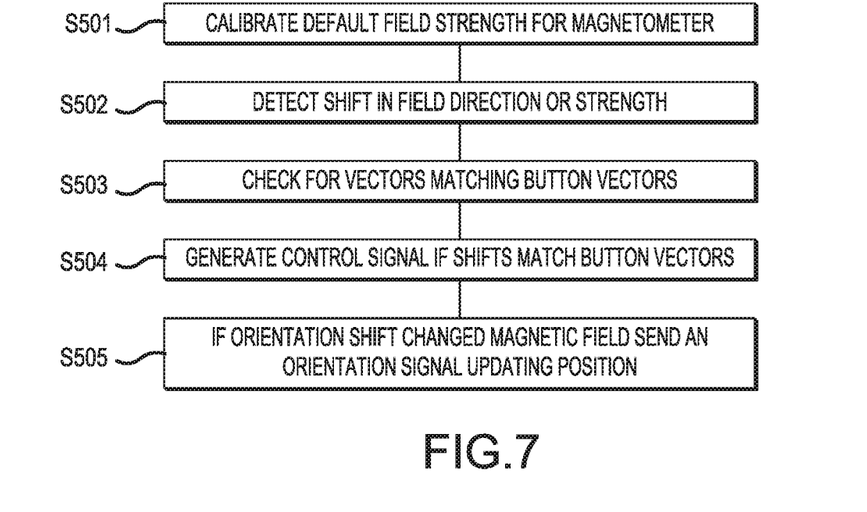
FIG. 7 is a process diagram for the filtering and correction process of the present invention.

The vector determination process performed by the control unit is outlined in FIG. 7 with a simple case of a single field shift. If multiple buttons are pressed, or the field has already been corrected, additional steps are necessary as described above regarding FIG. 5. First, the control unit is calibrated in S501 to detect the default magnetic field strength of the Earth in a horizontal position of the endoscope. Then, the control unit 25 detects a shift from this calibrated vector at S502. The control unit then attempts to match the detected shift with stored shifts/vectors corresponding to specific buttons to determine if one or more buttons have been activated in S503.

If one or more buttons have been pushed, then the control unit 25 generates a control signal corresponding to the button being pressed at S504. Finally, if after filtering for the button press, a field shift remains that is the result of an orientation change, the control unit calculates a corresponding control signal and transmits the calculated control signal to the appropriate peripheral device in S505.

As noted previously, the detected field shifts can also be compared with a set of deflection vectors corresponding to actuation of specific buttons and button combinations. This type of filtering and detection is particularly useful in hysteresis to detect fields that are rapidly shifting due to actuation of separate buttons. The magnetometer is subject to outside field influences and requires automated recalibration when the system returns to a state where no buttons are actuated.

In addition to the hysteresis provided for the detector, the rotation adjustment should also be tightly controlled by hysteresis so that the image displayed does not shift too much and cause dizziness in the user. Other controls, such as the button controls need not be so tightly controlled because they require active actuation. In contrast, the rotation of the endoscope may simply be the result of the user shifting position or the patient shifting position (e.g., breathing) and thus should be tightly controlled by hysteresis.

The orientation tracking system of the control unit 25 is also applicable to an externally applied IMU attached to the endoscope housing 11. In addition, the orientation tracking is also applicable to button systems that are not magnet based. In particular, the hysteresis control of the rotation would be applicable if magnet-based buttons are not used. For these applications, less calibration steps would be required, but the field shift detection algorithms would remain the same for the control unit 25.

The invention being thus described, it will be obvious that the same may be varied in many ways. Such variations are not to be regarded as a departure from the scope of the invention, and all such modifications as would be obvious to one skilled in the art are intended to be included within the scope of the following claims.

What is claimed is:

1. A control interface and adjustment mechanism for an endoscope or exoscope, comprising:
    at least one button comprising:
        a touch surface; and
        a magnet disposed adjacent to the touch surface;
    an inertial measurement unit configured to measure a rotation of the endoscope or exoscope including a magnetometer detecting ambient magnetic fields; and
    a control processor configured to receive signals from the magnetometer, wherein the control processor is configured to be connected to at least one peripheral component and controls the at least one component,
    wherein the control processor is configured to filter received first field information from the magnetometer to determine if the received first field information matches a specific stored button vector of at least one button vector stored in memory, the specific stored button vector comprising an average magnetic shift when the at least one button is depressed, and
    wherein if the received first field information matches the specific stored button vector, the at least one peripheral component is controlled based on the first field information received by the control processor.

2. The control interface and adjustment mechanism of claim 1, wherein the average magnetic field shift is mapped to the first field information by a delta function.

3. The control interface and adjustment mechanism of claim 1, wherein the average magnetic field shift is mapped to the first field information by a delta function based on orientation data received at the control processor from a gyroscope and/or an accelerometer.

4. The control interface and adjustment mechanism of claim 1, wherein the magnet of the at least one button is depressed when the touch surface is pressed by a user, the magnet being depressed such that the magnetometer detects a magnetic field shift as part of the first field information.

5. The control interface and adjustment mechanism of claim 1, wherein the inertial measurement unit further comprises a gyroscope and an accelerometer connected to the control processor,
  wherein the gyroscope provides orientation signals to the control processor, and
  wherein the orientation signals are corrected based on ambient magnetic fields detected by the magnetometer.

6. The control interface and adjustment mechanism of claim 1, wherein the average magnetic field shift is calculated from multiple button depressions detected when the magnetometer is in a calibration position.

7. The control interface and adjustment mechanism of claim 1, wherein, if the first field information does not match the specific stored button vector, the first field information is ignored or interpreted as movement of the endoscope or exoscope and the control processor does not send a control signal for controlling the at least one peripheral component based on the field information when the first field information does not match the specific stored button vector.

8. The control interface and adjustment mechanism of claim 1, further comprising a second button,
  wherein the at least one button and second button have corresponding specific stored button vectors.

9. The control interface and adjustment mechanism of claim 8, wherein, if the at least one button and second button are activated substantially simultaneously, the control processor determines that the two buttons were pressed by matching a sum of the specific stored button vector for each button with the first field information.

10. The control interface and adjustment mechanism of claim 1, wherein the at least one peripheral component includes: a camera, an internal lighting system, an external lighting system, an image storage system, a CCD/CMOS sensor, a zoom lens, a zoom actuator, a focus lens, a focus actuator, a camera panning motor, an irrigation pump, and/or a moveable camera head.

11. The control interface and adjustment mechanism of claim 1, wherein the at least one button is disposed entirely outside of a sealed housing of the endoscope or exoscope.

12. An endoscope comprising:
  a sealed housing;
  a control interface and adjustment mechanism, comprising:
    at least two buttons, each of the at least two buttons comprising:
      a touch surface; and
      a magnet disposed adjacent to the touch surface;
    an inertial measurement unit configured to measure a rotation of the endoscope or exoscope including a magnetometer detecting ambient magnetic fields; and
    a control processor configured to signals from the magnetometer, wherein the control processor is connected to at least one endoscope component and controls the at least one endoscope component,
    wherein the control processor is configured to filter received first field information from the magnetometer to determine if the received first field information matches a specific stored button vector of at least one button vector stored in memory, the specific stored button vector comprising an average magnetic shift when the one of the at least two buttons is depressed, and
    wherein, if the received first field information matches the specific stored button vector, the at least one endoscope component is controlled based on the first field information received by the control processor.

13. The endoscope according to claim 12, wherein the wherein the average magnetic field shift is mapped to the first field information by a delta function based on orientation data.

14. The endoscope according to claim 12, wherein the at least two buttons are disposed entirely outside of the sealed housing.

15. The endoscope according to claim 12, wherein the inertial measurement unit is equidistant from sides of the endoscope or exoscope.

16. A control interface and adjustment mechanism for an endoscope or exoscope, comprising:
  at least one button comprising:
    a touch surface; and
    a magnet disposed adjacent to the touch surface;
  a magnetometer detecting ambient magnetic fields; and
  a control processor receiving signals from the magnetometer, wherein the control processor is configured to be connected to at least one peripheral component and controls the at least one component,
  wherein the control processor filters received first field information from the magnetometer to determine if the received first field information matches a specific stored button vector of at least one button vector stored in memory, the specific stored button vector comprising an average magnetic shift when the at least one button is depressed,
  wherein if the received first field information matches the specific stored button vector, the at least one peripheral component is controlled based on the first field information received by the control processor, and
  wherein an average magnetic field shift is mapped to the first field information by a delta function based on orientation data received at the control processor from a gyroscope and/or an accelerometer.

17. A control interface and adjustment mechanism for an endoscope or exoscope, comprising:
  at least one button comprising:
    a touch surface; and
    a magnet disposed adjacent to the touch surface;
  a magnetometer detecting ambient magnetic fields;
  a control processor receiving signals from the magnetometer, wherein the control processor is configured to be connected to at least one peripheral component and controls the at least one component;
  a gyroscope connected to the control processor, the gyroscope providing orientation signals to the control processor; and
  an accelerometer connected to the control processor,
  wherein the orientation signals are corrected based on ambient magnetic fields detected by the magnetometer,
  wherein the control processor filters received first field information from the magnetometer to determine if the received first field information matches a specific stored button vector of at least one button vector stored in memory, the specific stored button vector comprising an average magnetic shift when the at least one button is depressed, and
  wherein if the received first field information matches the specific stored button vector, the at least one peripheral component is controlled based on the first field information received by the control processor.

18. A control interface and adjustment mechanism for an endoscope or exoscope, comprising:
  at least one button comprising:
    a touch surface; and
    a magnet disposed adjacent to the touch surface;

a magnetometer detecting ambient magnetic fields; and a control processor receiving signals from the magnetometer, wherein the control processor is configured to be connected to at least one peripheral component and controls the at least one component, wherein the control processor filters received first field information from the magnetometer to determine if the received first field information matches a specific stored button vector of at least one button vector stored in memory, the specific stored button vector comprising an average magnetic shift when the at least one button is depressed, wherein if the received first field information matches the specific stored button vector, the at least one peripheral component is controlled based on the first field information received by the control processor, wherein, if the first field information does not match the specific stored button vector, the first field information is ignored or interpreted as movement of the endoscope or exoscope and the control processor does not send a control signal for controlling the at least one peripheral component based on the field information when the first field information does not match the specific store button vector.

* * * * *